US008999472B2

(12) United States Patent
Hood et al.

(10) Patent No.: US 8,999,472 B2
(45) Date of Patent: *Apr. 7, 2015

(54) TUBULAR CONDUIT

(71) Applicant: Vascular Flow Technologies Limited, Dundee (GB)

(72) Inventors: Robert Gordon Hood, Longforgan (GB); Craig McLeod Duff, Tayside (GB)

(73) Assignee: Vascular Flow Technologies Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/674,131

(22) Filed: Nov. 12, 2012

(65) Prior Publication Data
US 2013/0144377 A1 Jun. 6, 2013

Related U.S. Application Data

(63) Continuation of application No. 10/599,136, filed as application No. PCT/GB2005/001102 on Mar. 23, 2005, now Pat. No. 8,389,088.

(30) Foreign Application Priority Data

Mar. 25, 2004 (GB) .................................. 0406719.5

(51) Int. Cl.
*B32B 1/08* (2006.01)
*A61F 2/06* (2013.01)
*F15D 1/06* (2006.01)
*A61F 2/07* (2013.01)
(Continued)

(52) U.S. Cl.
CPC . *A61F 2/06* (2013.01); *F15D 1/065* (2013.01); *A61F 2/07* (2013.01); *A61F 2/88* (2013.01); *A61F 2002/068* (2013.01); *A61F 2002/072* (2013.01); *B29C 45/14622* (2013.01)

(58) Field of Classification Search
USPC ........................ 428/36.9, 34.1; 623/1.33, 1.13
See application file for complete search history.

(56) References Cited

U.S. PATENT DOCUMENTS 4,629,458 A 12/1986 Pinchuk
5,556,426 A * 9/1996 Popadiuk et al. ............ 623/1.33
(Continued)

FOREIGN PATENT DOCUMENTS

DE 2520998 A1 11/1976
EP 1312321 A2 5/2003
(Continued)

OTHER PUBLICATIONS

Baugh J. A. et al., Flexible Auger, IBM Technical Disclosure Bulletin, vol. 19, No. 10, Mar. 1977, p. 3665, XP001173675, ISSN: 0018-8689, IBM Corp. New York, USA.

*Primary Examiner* — Ellen S Wood
(74) *Attorney, Agent, or Firm* — Kaplan Breyer Schwarz & Ottesen, LLP

(57) ABSTRACT

A tubular conduit is disclosed. The tubular conduit comprises a tubular portion made from a flexible material and an axially extending external helical formation located around the outside of the tubular portion. The external helical formation is for supporting the tubular portion. Optionally the tubular portion also comprises an axially extending internal helical protrusion, which imparts a helical flow to a fluid passing through the tubular portion. It is preferred that the tubular conduit is a vascular graft.

15 Claims, 2 Drawing Sheets

(51) Int. Cl.
*A61F 2/88* (2006.01)
*B29C 45/14* (2006.01)

(56) References Cited

U.S. PATENT DOCUMENTS

| | | |
|---|---|---|
| 5,609,624 A | 3/1997 | Kalis |
| 5,827,327 A | 10/1998 | McHaney et al. |
| 5,989,230 A | 11/1999 | Frassica |
| 6,312,458 B1 * | 11/2001 | Golds .................. 623/1.13 |
| 6,361,558 B1 | 3/2002 | Hieshima et al. |
| 2002/0169499 A1 * | 11/2002 | Zilla et al. ................. 623/1.15 |
| 2002/0179166 A1 | 12/2002 | Houston et al. |
| 2003/0120257 A1 | 6/2003 | Houston et al. |
| 2003/0225453 A1 | 12/2003 | Murch |
| 2004/0037986 A1 | 2/2004 | Houston et al. |
| 2007/0021707 A1 | 1/2007 | Caro et al. |

FOREIGN PATENT DOCUMENTS

| | | |
|---|---|---|
| WO | 0128746 A1 | 4/2001 |
| WO | 0189419 A1 | 11/2001 |
| WO | 03053495 A2 | 7/2003 |

* cited by examiner

TUBULAR CONDUIT

CROSS-REFERENCE TO RELATED APPLICATIONS

This application is a Continuation of and claims priority to U.S. patent application Ser. No. 10/599,136 with a U.S. filing date of Sep. 20, 2006, which in turn claims priority to International Application Serial Number PCT/GB2005/001102 filed on Mar. 23, 2005, and Great Britain Application Number 0406719.5 filed on Mar. 25, 2004. Furthermore, U.S. patent application Ser. No. 10/599,136 is incorporated herein by reference.

FIELD OF THE INVENTION

The present invention relates to a tubular conduit and to methods of making a tubular conduit. The present invention also relates to a mould for a tubular conduit.

BACKGROUND OF THE INVENTION

It is known in the art to provide vascular grafts as artificial vascular prostheses to be implanted in individuals with diseased blood vessels. For example, if an individual is suffering from atherosclerosis then a section of blood vessel may be replaced with a vascular graft.

The problem with such vascular grafts is that they have a tendency to cause turbulence in the flow of the blood that they carry, particularly at the join between the vascular graft and the blood vessel at either end. This can result in plaque formation, reduced flow capacity and thromboses in the blood vessel.

WO-A-00/38591 discloses a vascular graft in which a tubular graft is provided with four equally spaced ridges on the interior of the graft. Each edge is in the form of an axially extending helix. The ridges induce helical flow to the blood passing through the vascular graft. The provision of a helical blood flow reduces the turbulence of the blood in the vascular graft which, in turn, reduces the likelihood of plaque formation, reduced flow capacity and thromboses.

WO-A-03/045278 discloses a method for introducing an internal helical formation into a vascular graft. The method comprises supporting a flexible tubular concertinaed material on a mandrel having a groove therein and placing a helical former corresponding to the groove around the material. This deforms the material to have an internal helical formation corresponding to the shape of the groove. The material is set in that configuration and the former and the mandrel can then be removed.

The problem with the method disclosed in WO-A-03/045278 is that, in practice, the method is quite slow and cannot readily form part of a production process.

A problem with vascular grafts, in general, whether or not they have an internal helical formation is that while vascular grafts are usually flexible, they do not exactly replicate the physical properties of the blood vessel that they replace. Normally, the vascular graft will follow a smooth curve when it is bent. However, if it is bent excessively then there is a risk that instead of forming a smooth curve it will form a kink, effectively blocking the cross-section of the vascular graft. If a kink occurs while the vascular graft is implanted then this can be very dangerous as blood flow is significantly reduced. This is particularly a problem if a helical formation is provided on the vascular graft as described in WO-A-03/04278 because the concertinaing of the vascular graft can tend to increase the likelihood of kinking taking place.

SUMMARY OF THE INVENTION

While the above problems have been described in relation to vascular grafts, it is to be appreciated that the problems are not limited thereto. Indeed, the problems of flow turbulence and kinking exist for any flexible tubular conduit through which a fluid flows. Therefore, the present invention is not limited to vascular grafts and also relates to other types of tubular conduits, including tubular grafts or implants in other parts of the body and tubular conduits not associated with the human body.

Accordingly the present invention seeks to alleviate one or more of the above problems.

According to one aspect of the present invention, there is provided a tubular conduit comprising: a tubular portion made from a flexible material; and an axially extending external helical formation located around the outside of the tubular portion for supporting the tubular portion.

Preferably, the tubular conduit further comprises an axially extending internal helical protrusion located around the inside of the tubular portion for imparting a helical flow to a fluid passing through the tubular portion.

Conveniently, the tubular conduit is for use as a graft, preferably as a vascular graft.

Advantageously, the internal helical protrusion comprises a section of the tubular portion deformed by an axially extending deformation helix.

Conveniently, the axially extending deformation helix is made from polyurethane.

Preferably, the axially extending deformation helix is sintered to the flexible material of the tubular portion.

Advantageously, the external helical formation has a different helix angle from the internal helical protrusion.

Conveniently, the helix angle of the external helical formation is greater than the helix angle of the internal helical protrusion.

Preferably, the helix angle of the internal helical protrusion is between 8° and 20°.

Advantageously, the helix angle of the external helical formation is greater than 50° and preferably between 65° and 80°.

Conveniently, the tubular portion is made from ePTFE.

Preferably, the external helical formation is made from polyurethane.

Advantageously, the inside of the tubular portion has a carbon coating.

Conveniently, the external helical formation is sintered to the flexible material of the tubular portion.

According to another aspect of the present invention, there is provided a method of making a tubular conduit comprising the steps of:
(a) providing a tubular portion made from a flexible material;
(b) flowing a moulding liquid in an axially extending, helical form around the exterior of the tubular portion; and
(c) solidifying the moulding liquid.

Preferably, step (b) comprises the step of flowing a moulding liquid in two axially extending helical forms around the exterior of the tubular portion.

Advantageously, the two helical forms each has a different helix angle.

Conveniently, step (b) comprises: (i) deforming the tubular portion so as to provide an internal helical protrusion on the inside of the tubular portion and a corresponding external helical groove; and (ii) flowing the moulding liquid into the external helical groove to form an axially extending helical form.

Preferably, the helix angle of the moulding liquid flowed into the external helical groove is less than the helix angle of the other axially extending helical form.

Advantageously, the helix angle of the moulding liquid flowed into the external helical groove is between 8° and 20°.

Conveniently, step (b) comprises locating the tubular portion over a mandrel; and encasing the tubular portion within a mould such that the tubular portion is sandwiched between the mandrel and the mould.

Preferably, the mandrel has an axially extending helical channel on its surface and wherein step (i) further comprises the step of introducing the moulding liquid between the tubular portion and the mould such that the moulding liquid deforms the tubular portion by pressing the tubular portion into the helical channel on the mandrel to provide the internal helical protrusion.

Advantageously, the method further comprises, between the steps of locating of the tubular portion over the mandrel and encasing the tubular portion within the mould, the step of: pushing the tubular portion at least partially into the helical channel on the mandrel.

Conveniently, the step of introducing the moulding liquid comprises injecting the moulding liquid into the mould above the helical channel in the mandrel.

Preferably, the mould has an axially extending helical channel about its inside surface and wherein step (b) further comprises the step of introducing the moulding liquid between the tubular portion and the mould such that the moulding liquid flows into the helical channel in the mould.

Advantageously, the helix angle of the helical channel in the mould is greater than 50°, and preferably is between 65° and 80°.

Conveniently, the method further comprises, between steps (b) and (c), the step of sintering the moulding liquid onto the flexible material of the tubular portion.

Preferably, step (b) is carried out between 600 and 800 kPa and between 170 and 210° C., more preferably at 689 kPa and 190° C.

Advantageously, the method further comprises the step of coating the inner surface of the tubular portion with carbon.

Conveniently, the moulding liquid is polyurethane.

Preferably, the flexible material is ePTFE.

According to a further aspect of the present invention, there is provided a mould for providing a helical formation onto a tubular conduit comprising:

a mandrel on which the tubular conduit is locatable; and
a moulding block having a bore for receiving the mandrel with the tubular conduit located thereon.

Conveniently, the mandrel has an axially extending helical channel on its inner surface.

Preferably, the bore has an axially extending helical channel on its inner surface.

Advantageously, wherein the helix angle of the helical channel on the bore is different from the helix angle of the helical channel on the mandrel.

Conveniently, the helix angle of the helical channel on the bore is greater than the helix angle of the helical channel on the mandrel.

Preferably, the helix angle of the helical channel on the mandrel is between 8° and 20°.

Advantageously, the helix angle of the helical channel on the bore is greater than 50° and preferably between 65° and 80°.

Conveniently, the tubular conduit is a vascular graft.

The terms "helix" and "helical" as are used to herein cover the mathematical definition of helix and helical and any combination of mathematical definitions of helical and spiral.

BRIEF DESCRIPTION OF THE DRAWINGS

In order that the present invention may be more readily understood and so that further features thereof may be appreciated, embodiments of the invention will now be described, by way of example, by reference to the accompanying drawings in which.

DETAILED DESCRIPTION

Figure 1:
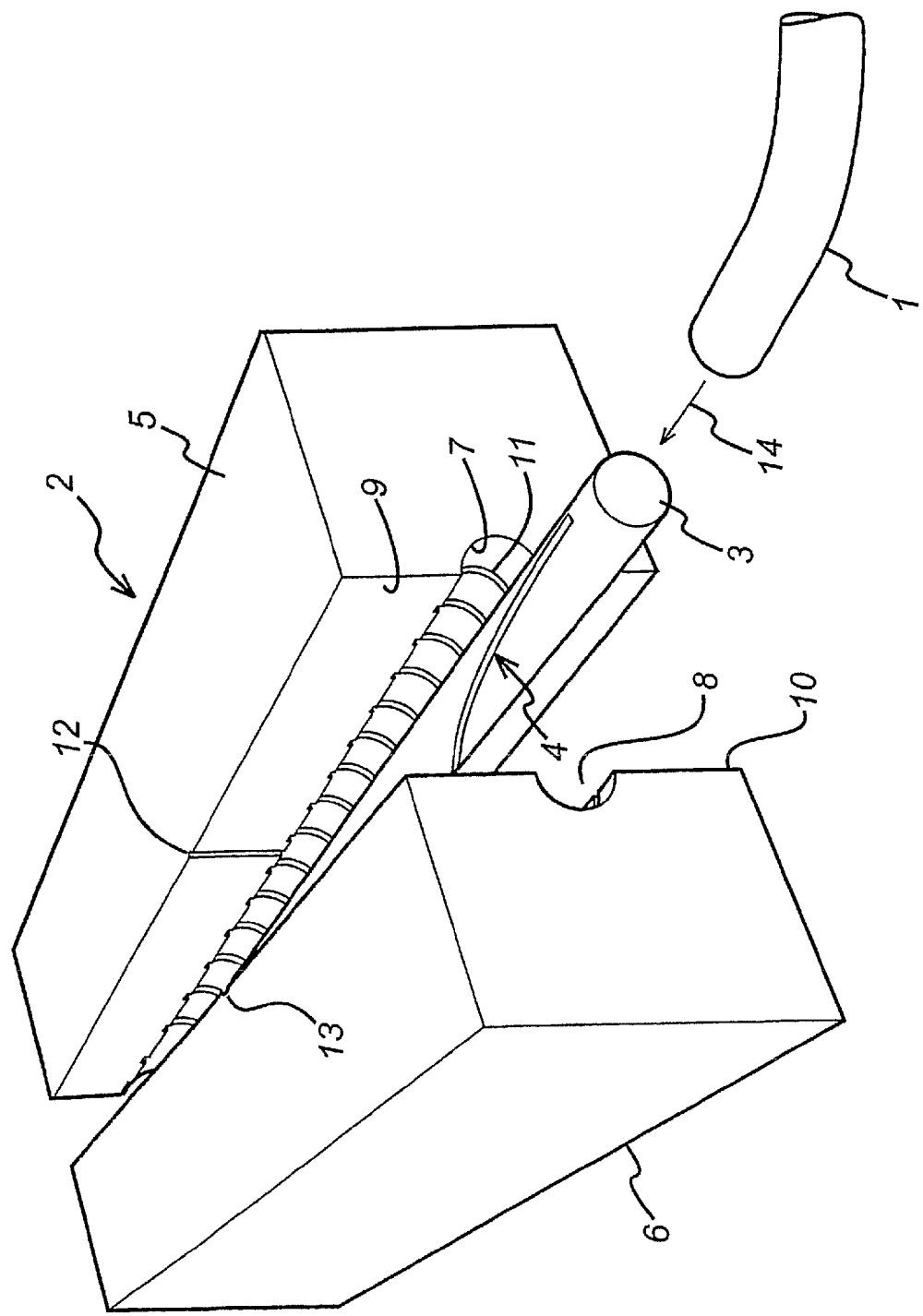
FIG. 1 is a perspective view of a vascular graft prior to a method of the present invention and the moulding equipment used in one embodiment of the present invention.

Referring to FIG. 1, a tubular conduit, namely a blank vascular graft 1 (that is to say, a vascular graft which has not yet had any helical formations formed on it) comprises a tubular portion made from expanded polytetrafluoroethylene (ePTFE). Consequently, the blank vascular graft 1 takes the form of a flexible hollow cylindrical tube.

In order to provide helical formations on the blank vascular graft 1, a mould 2 is provided comprising a mandrel 3. The mandrel 3 is an elongate cylinder having an axially extending helical channel 4 in its outer surface. The helical channel 4 has a helix angle of between 8° and 20°. In this embodiment the length of the mandrel 3 and the helix angle of the helical channel 4 are chosen such that the helical channel 4 forms one complete helical turn from one end of the mandrel 3 to the other. In alternative embodiments, the helical channel 4 forms more or less than one helical turn. For example, in some embodiments the helical channel 4 makes two complete helical turns.

The mould 2 also comprises first and second mould block halves 5, 6. Each mould block 5, 6 is cuboidal and has a semi-circular channel 7, 8 extending in an axial direction along one long side 9, 10 of the cuboidal block 5, 6. The semi-circular channels 7, 8 are sized and located such that when the two mould blocks 5, 6 are adjacent one another, the two semi-circular channels 5, 6 form a cylindrical bore in which the mandrel 3 can be received with just enough space remaining for the presence of the vascular graft 1.

On the inside surface of the semi-circular channel 7, 8 on each of the mould blocks 5, 6 there is provided a series of arcuate grooves 11 which are arranged such that when the mould blocks 5, 6 are adjacent one another, the arcuate groove 11 on either mould block 5, 6 join to form a single helical channel, extending in an axial direction, about the interior of the bore that is formed. The helix angle of the helical channel in the mould blocks 5, 6 is greater than 50° and is preferably between 65° and 80°. Thus the helix angle of the helical channel formed in the mould blocks 5, 6 is different from and, indeed, greater than the helix angle of the helical channel in the mandrel 3.

An injection channel 12, 13 is provided in each of the mould blocks 5, 6 leading from their respective semi-circular channel 7, 8 to the exterior of the mould blocks 5, 6. The injection channels 12, 13 are arranged such that when the mould blocks 5, 6 are adjacent one another, the two injection channels 12, 13 are aligned to form a single injection hole leading from the cylindrical bore to the exterior of the mould 2.

Means are provided (not shown) to lock the two mould blocks 5, 6 together in the configuration whereby the cylindrical bore and the injection hole are formed. In some embodiments the means comprise retaining screws.

In order to finish the blank vascular graft 1, the mould 2 is heated. In this embodiment, the mould 2 is heated to 190° C. but the exact temperature used in each embodiment is dependent upon the materials that are used in the process.

The two mould blocks 5, 6 and the mandrel 3 are separated from one another.

The blank vascular graft 1 is then fitted on to the mandrel 3 in the direction of the arrow 14 in FIG. 1. The vascular graft 1 is partially pushed into the helical channel 4 in the surface of the mandrel 3. In some embodiments, this is carried out using a spatula.

The mandrel 3, with the vascular graft 1 on it, is then placed within the two semi-circular channels 7, 8 in the mould blocks 5, 6 such that the injection hole formed by the injection channels 12, 13 is aligned with the helical channel 4 in the surface of the mandrel 3. Because the vascular graft 1 has been partially pushed into the helical channel 4 in the surface of the mandrel 3, it is possible to ensure this alignment visually. The two mould blocks 5, 6 are then held tightly together, for example, by retaining screws.

It is to be appreciated that the mandrel 3, the cylindrical bore formed by the two semi-circular channels 7, 8 and the vascular graft 1 are sized such that the vascular graft 1 is tightly sandwiched between the two mould blocks 5, 6 and the mandrel 3.

The mould 2, together with the vascular graft 1, are then placed in a pressurisable injection moulding machine. In this embodiment, the pressure is raised to 100 Psi (689 kPa) but the optimum pressure to be used in each embodiment is dependent upon the materials used.

Molten polyurethane is injected via the injection hole formed by the injection channels 12, 13 into the interior of the mould 2. The molten polyurethane deforms the vascular graft 1 by pressing it into the helical channel 4 in the mandrel 3 to create a helical protrusion 15 (see FIGS. 2 and 3) on the inside surface of the vascular graft 1. It simultaneously creates a helical groove in the outside surface of the vascular graft 1 into which the molten polyurethane flows.

The molten polyurethane also flows along the helical channel formed by the arcuate grooves 11 in the mould blocks 5, 6. Thus only a single injection of molten polyurethane is required in order to fill both the helical groove in the outside surface of the vascular graft 1 and the helical channel in the mould blocks 5, 6.

The heat and pressure sinters the polyurethane onto the ePTFE vascular graft 1. The mould 2 is then opened and the vascular graft 1 removed from the mandrel 3 and allowed to cool.

Figure 2:
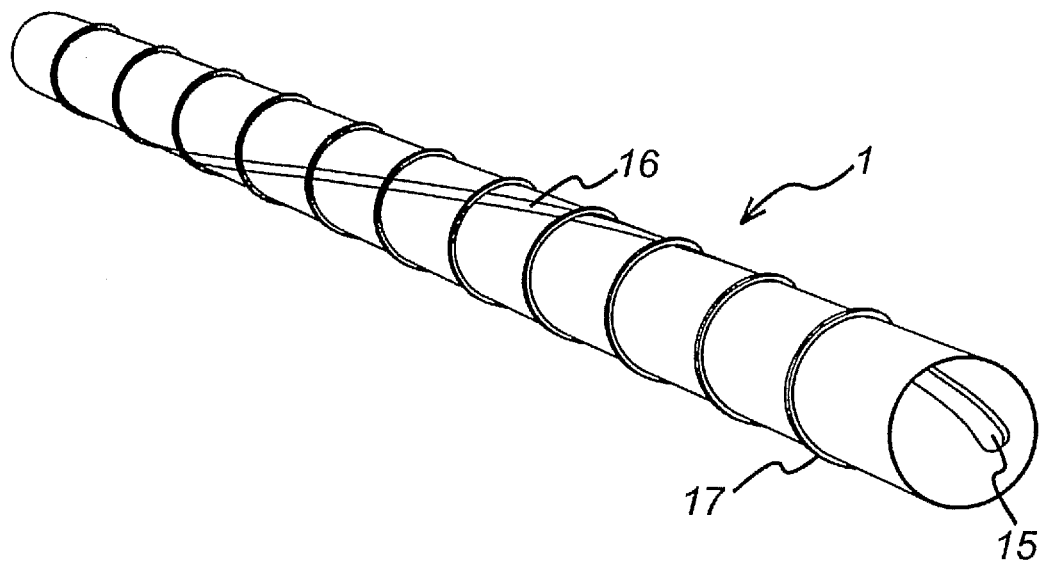
FIG. 2 is a perspective view of a vascular graft in accordance with one embodiment of the present invention.
Figure 3:
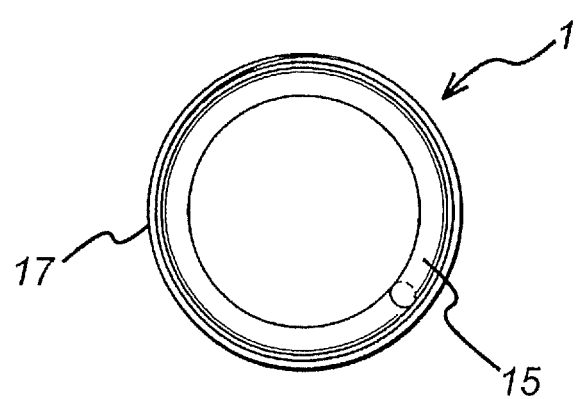
FIG. 3 is a cross-sectional view of the embodiment shown in FIG. 2.

Thus, as is shown in FIGS. 2 and 3, there are two helical formations formed in polyurethane on the vascular graft 1. There is firstly a polyurethane deformation helix 16 whose outer surface lies substantially flush with the outer surface of the vascular graft 1 and which deforms the vascular graft 1 so as to provide the internal helical protrusion 15. The deformation helix 16 is formed by the helical channel 4 on the mandrel 3 and so has the same helix angle as that channel, namely between 8° and 20°. Secondly, there is a support helix 17, which winds around the exterior of the vascular graft 1 and sits slightly proud of the rest of the outer surface of the vascular graft 1. The support helix 17 is formed by the helical channel in the bore of the mould blocks 5, 6 and so has the same helix angle as that channel, namely greater than 50° and preferably between 65° and 80°. Thus the helix angle of the support helix 17 is different from and, indeed, greater than the helix angle of the deformation helix 16 and internal helical protrusion 15.

It has been found that when using polyurethane to form the deformation and support helices 16, 17 and ePTFE to form the vascular graft 1, the combination of 100 Psi (689 kPa) moulding pressure, and 190° C. operating temperature provides an optimum combination for the sintering step. In particular, the vascular graft 1 is not overly deformed and molten polyurethane flow is maximised, bringing the moulding time to the minimum of 5 seconds. Consequently, the vascular graft 1 is finished with the two polyurethane helices 16, 17 formed on it quickly and easily.

In order to be used, the finished vascular graft 1 is implanted into a patient usually by a surgeon, as is known in the art.

If necessary, the surgeon can strip back the support helix 17 from the remainder of the vascular graft 1 before or after implantation. This is useful if, for example, the vascular graft 1 must be implanted in a space or configuration in the patient where it will not fit with the support helix 17 in place.

It is to be noted that the internal helical protrusion 15 influences the flow of blood which passes through the vascular graft when in use. Furthermore, the external support helix 17 maintains the shape of the vascular graft 1, allowing it to flex but greatly reducing the risk of a kink forming.

The above embodiment has been described in which both a deformation helix 16 and a support helix 17 are provided on the vascular graft 1. However, it is to be appreciated that by removing the helical groove 4 from the mandrel 3, a vascular graft 1 is produced that has the support helix 17 but which does not have the deformation helix 16 on it. Consequently, the vascular graft 1 does not have an internal helical protrusion 15. Conversely, in further embodiments, the arcuate grooves 11 are not included in the moulding blocks 5, 6 and so the deformation helix 16 and internal helical protrusion 15 are provided but the support helix 17 is not formed on the vascular graft 1.

In preferred embodiments of the present invention, a carbon coating is applied to the interior surface of the vascular graft 1. The advantage of adding the carbon coating is that it enhances the biocompatibility and tissue response for the graft. Processes for carbon coating inside the vascular graft 1 are known in the art.

The size of the vascular graft 1 is dependent upon the blood vessel which it is intended to replace. Typically, the diameter of the vascular graft is between 4 mm and 12 mm when replacing a peripheral blood vessel and between 18 mm and 40 mm when replacing a non-peripheral blood vessel. Vascular grafts outside these ranges of diameter are nevertheless within the scope of the present invention.

In the above described embodiments, the vascular graft 1 is made from ePTFE and the helical formations 16, 17 are made from polyurethane. However, in other embodiments of the invention, different materials are selected in order to take advantage of particular properties of those materials. For example instead of using polyurethane, another moulding material, such as polyester or PTFE, that can be injected in liquid form and then solidified is used in some embodiments. Similarly, in some embodiments the blank vascular graft 1 is made from a fabric such as a knitted, woven or extruded polymer. In some embodiments the blank vascular graft 1 and the moulding material consist of the same, or similar, materials such as ePTFE and PTFE, respectively, or both consisting of polyurethane.

What is important is that the injected moulding material should have a melting temperature lower than the melting temperature of the material from which the vascular graft 1 is made.

It is to be appreciated that in the above described embodiments of the invention the conditions of 689 kPa and 190° C. are referred to merely as the optimum conditions when the blank vascular graft 1 is made from ePTFE and polyurethane is injected to form the deformation helix 16 and the support helix 17 and with the mould 2 as described. However, the optimum conditions will be different in alternative embodiments. In particular, the optimum conditions are dependent on the mould conditions and on the material from which the blank vascular graft is made and on the injected material used. Nevertheless, a generally preferred range of conditions is from 600 to 800 kPa and from 170° to 210° C.

In some alternative embodiments, the vascular graft 1 is provided with more than one deformation helix 16 and internal helical protrusion 15 and/or more than one support helix 17. In these embodiments, it is preferred that the multiple helices be equally spaced about the circumference of the vascular graft 1.

While the above embodiments of the present invention have been described in relation to vascular grafts, in other embodiments of the invention different tubular conduits are provided. For example, in some embodiments of the invention, the tubular conduit is a non-vascular graft. In other embodiments of the invention the tubular conduit is not a graft at all but is, for example, a hose pipe, a hose leading to or from a dishwasher or washing machine, or a petrol pump hose or the like. In all of these embodiments, the tubular conduit comprises a tubular portion made from a flexible material. The provision of an external helical formation located around the outside of the tubular portion reduces the possibility of kinking in the tubular portion occurring while permitting flexibility in the tubular portion. The provision of an internal helical protrusion around the inside of the tubular portion imparts a helical flow to a fluid passing through the tubular portion. In some embodiments only the external helical formation or the internal helical protrusion is provided but in other embodiments, both the external helical formation and the internal helical protrusion are provided. The tubular portion need not be of precisely circular cross-section, although that is most preferred, but the cross-section should preferably be such as to avoid excessive turbulence in the flow of fluid passing through it.

EXAMPLES

The present invention is now further illustrated by way of the following examples.

Example 1

Production of ePTFE Graft

Materials
Standard ePTFE grafts
Ab100 Injection moulding machine
Chronoflex Polyurethane (PU)
Injection mould former
P3 Mandrel
Oven
Protective gloves
Air compressor
Preparation
All materials were cleaned down thoroughly with IPA prior to use.
Protective equipment (hair net, gloves lab coats and masks) was worn by all personnel in the immediate vicinity.
The Ab 100 injection moulding machine was switched on and the machine allowed to rise to the required temperature of 196° C. (385° F.).
The Chronoflex was dried in the oven at 160° C. for 30 mins prior to injection and then loaded into the storage chamber on the injection-moulding machine.
The injection chamber was then filled with Chronoflex to just below the surface.
The P3 mandrel and the injection mould were placed into the oven (alongside the Chronoflex) which had been set at 160° C.
The mandrel and injection mould were allowed to heat up for 30 mins.
The pressure gauge on the Ab 100 machine was checked to ensure that it reached 100 Psi (689 kPa). The compressor was used if the pressure was too low.
Once all settings had been reached, the mandrel and mould were removed from the oven (wearing the protective gloves) and the required length of ePTFE graft was placed onto the mandrel.
A spatula was used to push the ePTFE material partially into the helical channel of the mandrel. This allowed the mandrel to be lined up correctly.
The mandrel was aligned in the mould so that the helical channel was in line with the injection hole.
The block was closed and tightened with retaining screws.
Injection
The mould was placed in the machine and the injection hole was aligned with the injecting nozzle.
The mould was clamped in place and as much molten PU (polyurethane) was injected as required.
The mould was unclamped and the retaining screws removed. The mandrel was then removed.
The ePTFE Graft was removed from the mandrel by gripping it (with a gloved hand) along its spiralled length and twisting and pulling gently (so as not to deform it).
The graft was placed in a sterile grip seal bag, then packaged appropriately and sterilised.

Example 2

Production of ePTFE Graft

Equipment Used
1. Polymer granules
2. E.P.T.F.E. material
3. Mould (either a long one of helix angle 8° (two complete helical turns) or a short one of helix angle 17° (one complete helical turn))
4. Mandrels (8°/17° as for the mould)
5. Injection moulding machine
6. Compressor
7. Scissors
8. Knife
9. Ruler
10. Gloves
11. Azo wipes
12. Tech wipes
13. Goggles
Preparation for Injecting
1. Goggles were worn.

2. The compressor was switched on and allowed to reach its operation pressure of 100 PSI (689 kPa).
3. The injection moulding machine was switched on and allowed to get up to operating temperature which is 190° C. (377 deg), and is maintained by a thermostat.
4. A hopper on the side of the injector was filled up with polymer granules (about ¾ full).
5. The injection chamber was filled up with granules just up to the top.
6. The granules were compressed in the chamber. Granules were added and compressed until level with the top.

Preparation for Moulding Block
1. The block and mandrel and also the screws were all cleaned down with azo wipes.
2. 30 cm of E.P.T.F.E. tubing was measured out and then put on the mandrel making sure to pull it up to the stop, at the end of the mandrel. Once this was achieved it was ensured that the material was smooth and not bunched up on the mandrel.
3. Once the material was on the mandrel, the mandrel was put in the moulding block making sure to put the dowel in the locating hole. The other half of the mould was placed on top and screwed down in a spiral sequence until all the crews were fully home. They were then tightened up with an allen key to make sure they were tight and there were no gap between the 2 halves.

Injection
Injection was carried out as described in Example 1.

The invention claimed is:

1. A tubular conduit comprising:
a tubular portion comprising an inside and an outside and being made from a flexible material;
an axially extending external helical formation located around the outside of the tubular portion for supporting the tubular portion; and
an axially extending internal helical protrusion located around the inside of the tubular portion for imparting a helical flow to a fluid passing through the tubular portion, having a different helix angle from the external helical formation;
wherein the axially extending internal helical protrusion comprises a section of the tubular portion deformed by an axially extending deformation helix; and
wherein the external helical formation and the axially extending deformation helix are made from the same material and are fused together.

2. The tubular conduit according to claim 1, for use as a graft.

3. The tubular conduit according to claim 2, wherein the graft is a vascular graft.

4. The tubular conduit according to claim 1, wherein the internal helical protrusion comprises a section of the tubular portion deformed by an axially extending deformation helix.

5. The tubular conduit according to claim 4, wherein the external helical formation and the axially extending deformation helix are made from polyurethane.

6. The tubular conduit according to claim 1, wherein the axially extending deformation helix is sintered to the flexible material of the tubular portion.

7. The tubular conduit according to claim 1, wherein the helix angle of the external helical formation is greater than the helix angle of the internal protrusion.

8. The tubular conduit according to claim 1, wherein the helix angle of the internal protrusion is between 8° and 20°.

9. The tubular conduit according to claim 1, wherein the helix angle of the external helical formation is greater than 50°.

10. The tubular conduit according to claim 9, wherein the helix angle of the external helical formation is between 65° and 80°.

11. The tubular conduit according to claim 1, wherein the tubular portion is made from ePTFE.

12. The tubular conduit according to claim 1, wherein the inside of the tubular portion has a carbon coating.

13. The tubular conduit according to claim 1, wherein the external helical formation is sintered to the flexible material of the tubular portion.

14. The tubular conduit according to claim 1, wherein the helix angle of the internal protrusion is between 8° and 20° and the helix angle of the external helical formation is between 65° and 80°.

15. The tubular conduit according to claim 1 wherein the external helical formation and the axially extending deformation helix are made from the same material and are fused together as a result of flowing a moulding liquid into axially extending helical forms around the exterior of the helical portion and solidifying the moulding liquids to form said same material.

* * * * *